(12) United States Patent
Menon

(10) Patent No.: US 8,895,569 B2
(45) Date of Patent: Nov. 25, 2014

(54) CARBOCYCLIC NUCLEOSIDES AND THEIR PHARMACEUTICAL USE AND COMPOSITIONS

(71) Applicant: Cellceutix Corporation, Beverly, MA (US)

(72) Inventor: Krishna Menon, North Reading, MA (US)

(73) Assignee: Cellceutix Corporation, Beverly, MA (US)

( * ) Notice: Subject to any disclaimer, the term of this patent is extended or adjusted under 35 U.S.C. 154(b) by 0 days.

(21) Appl. No.: 13/730,247

(22) Filed: Dec. 28, 2012

(65) Prior Publication Data

US 2014/0200229 A1    Jul. 17, 2014

Related U.S. Application Data

(60) Provisional application No. 61/582,550, filed on Jan. 3, 2012.

(51) Int. Cl.
| | | |
|---|---|---|
| *A61K 31/52* | (2006.01) | |
| *C07D 473/34* | (2006.01) | |
| *C07D 473/16* | (2006.01) | |
| *C07D 473/00* | (2006.01) | |

(52) U.S. Cl.
CPC ............ *C07D 473/16* (2013.01); *C07D 473/00* (2013.01); *A61K 31/52* (2013.01)
USPC ........................................ 514/263.2; 544/277

(58) Field of Classification Search
CPC .............................. A61K 31/52; C07D 473/34
USPC ........................................ 514/263.2; 544/277
See application file for complete search history.

(56) References Cited

FOREIGN PATENT DOCUMENTS

| | | | |
|---|---|---|---|
| EP | 0 349 242 | A1 | 1/1990 |
| EP | 0 349 242 | A2 | 1/1990 |

OTHER PUBLICATIONS

Mason, J., et al: "Topical preparations for the treatment of psoriasis: a systemic review", British Journal of Dermatology, Oxford: Willy—Blackwell, UK, vol. 146, No. 3, Mar. 1, 2002; p. 351-364, XP002244836: ISSN: 0007-0963.
PCT International Search Report for International Application PCT/US2012/072103, mailed Apr. 15, 2013.
International Preliminary Report on Patentability dated Jul. 8, 2014 for corresponding International Application PCT/US2012/072103.
Search Report of Taiwan Patent Application No. 101151185.
English Translation of Search Report of Taiwan Patent Application 101151185.
Anne M. Exall, et al., "Synthesis from (-)-Aristeromycin and X-Ray Structure of (-)- Carbovir". J. Chem. Soc. Perkin Trans. 1, 1991, 2467-2477.
Horatio F. Olivo, et al. "Enantioselective syntheses of 5'-*homo*-carbocyclic nucleosides" Tetrahedron: Assymmetry, 1997, 8, 3785-3788.

*Primary Examiner* — Raymond Henley, III
(74) *Attorney, Agent, or Firm* — Ladas & Parry LLP

(57) ABSTRACT

Disclosed are compounds of the formula I

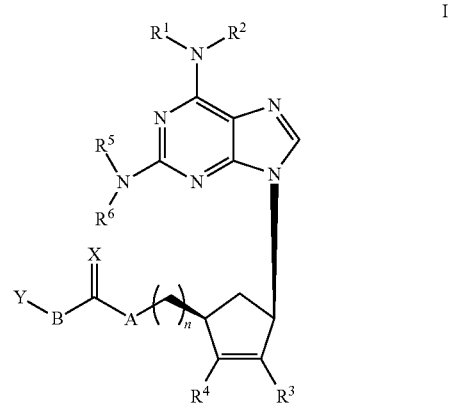

and the pharmaceutically acceptable salts of such compounds. Also disclosed are processes for the preparation of such compounds, intermediates used in the preparation of such compounds, and the uses of such compounds in treating inflammatory skin diseases.

21 Claims, 8 Drawing Sheets

Prurisol

CARBOCYCLIC NUCLEOSIDES AND THEIR PHARMACEUTICAL USE AND COMPOSITIONS

CROSS REFERENCE APPLICATION

This application claims the benefit of U.S. Provisional Patent Application No. 61/582,550 filed Jan. 3, 2012, the content of which is incorporated herein by reference.

BACKGROUND OF THE INVENTION

The present invention relates to carbocyclic nucleosides and the pharmaceutically acceptable salts thereof, processes for the preparation of such compounds, intermediates used in the preparation of such compounds, pharmaceutical compositions comprising such compounds, and the uses of such compounds in treating inflammatory skin diseases, including, but not limited to, psoriasis, eczema and seborrhiasis.

The aforementioned carbocyclic nucleosides and the pharmaceutically acceptable salts thereof, when administered to a patient, are capable of producing, directly or indirectly, anti-inflammatory compounds. Such a compound may be produced by hydrolysis or it may be a metabolite. These compounds are, therefore, useful in the treatment of psoriasis and other inflammatory skin diseases. There is currently great interest in finding new therapies for the foregoing diseases.

In one embodiment, the present invention relates to compounds, pharmaceutical compositions and methods for the treatment of psoriasis. Psoriasis is a chronic, autoimmune disease that appears on the skin. In psoriasis, the growth cycle of skin cells is accelerated by faulty immune signals, but the exact cause of the disease is not known. The research studies in this area suggest that increased proliferation and hyperplasia of the epidermal cells are implicated in the pathogenesis of psoriasis [Anderson et. al., Pathogenesis of skin disease, 67 (1986)]. Psoriasis is also considered to be an inflammatory skin disease in which neutrophils are associated with psoriatic lesions. Also, higher levels of arachidonic acid in the psoriatic plaques than in normal tissues are also reported in the literature. The metabolites of arachidonic acid play an important role in psoriasis because they are vasodilators and chemoattractants for neutrophils. It is also known that in the psoriatic lesions, Psoriasis Susceptibility-related RNA Gene Induced by Stress (PRINS), 12R-lipoxygenase and IL-20 activities are increased significantly. The enhanced proliferation of keratinocytes in the psoriatic plaques is also documented in the literature. It has been found that in psoriatic lesions, cyclic adenosine monophosphate (cAMP) levels are decreased, which may be result in diminished regulation of cell division due to less activation of the protein kinase. These studies further suggest that psoriasis is not merely a disease of the epidermis [Farber et. Al., Psoriasis: a disease of the total skin. J. Am. Acad. Dermat. 12, 150 (1985); Powrie et. al. J. Cxp. Med. 179, 589 (1994)].

Psoriasis is a prevalent disease, and it has been estimated that approximately 3% of the population of the world is suffering from psoriasis. This includes 2.2% of the population of the United States of America alone. It is a worthwhile goal to develop novel drugs for the treatment of this chronic disease. A wide variety of non-specific drugs such as lithium, β-blockers, antimalarials, corticosteroids and nonsteroidal anti-inflammatory agents have been investigated for the control of psoriasis [Abel et. al., J. Am. Acad. Dermatol. 15, 1007 (1986)], however, there are no specific drugs in the market for this disease.

The compounds currently commercially available for the treatment of psoriasis suffer from one or more deficiencies, including side effects, lack of sufficient efficacy and an inconvenient or non-esthetic method of administration. Accordingly, the search for effective treatments continues. The present invention relates to new and effective compounds for the treatment of psoriasis and other inflammatory skin diseases.

Animal models for the evaluation of the efficacy of drug molecules for the treatment of psoriasis are well established [Schon et. al., Nature Med. 3, 183-188 (1997); Wrone-Smith et. al., J. Clin. Invest. 98, 1878-1887 (1996); Christofidou-Solomidou et. al., J. Am. Pathol. 150, 631-639 (1997); Nickoloff et. al., J. Invest. Dermatol. 108, 539 (1997); Prens et. al. Clin. Dermatol. 13, 115-129 (1995); Carroll et. al., Cell 83, 957-968 (1995); Sundberg et. al., Handbook of Mouse Mutations with Skin and Hair Abnormalities, 253-268 (1994); Boehncke et. al., Arch. Dermatol. Res. 286, 325-330 (1994) and Boehncke et. al., Nature 379, 777 (1996)].

Abacavir, (−) cis-[4-[2-amino-6-cyclopropylamino)-9H-purin-9-yl]-2-cyclopenten-yl]-1-methanol, a carbocyclic nucleoside which possesses a 2,3-dehydrocyclopentene ring, is referred to in U.S. Pat. No. 5,034,394 as a reverse transcriptase inhibitor. Recently, a general synthetic strategy for the preparation of this type of compound and intermediates was reported [Crimmins, et. al., J. Org. Chem., 61, 4192-4193 (1996) and 65, 8499-8509-4193 (2000)]. As discussed in greater detail below, in a particular embodiment, the present invention relates to novel esters of abacavir, including, but not limited to (−) cis-[4-[2-amino-6-(cyclopropylamino)-9H-purin-9-yl]-2-cyclopentene-1-hydroxymethyl acetate (also referred to herein as Prurisol) and the pharmaceutically acceptable salts thereof. Prurisol is an orally bioavailable compound for the treatment of inflammatory skin diseases such as psoriasis, eczema and seborrhiasis.

SUMMARY OF THE INVENTION

Figure 1:
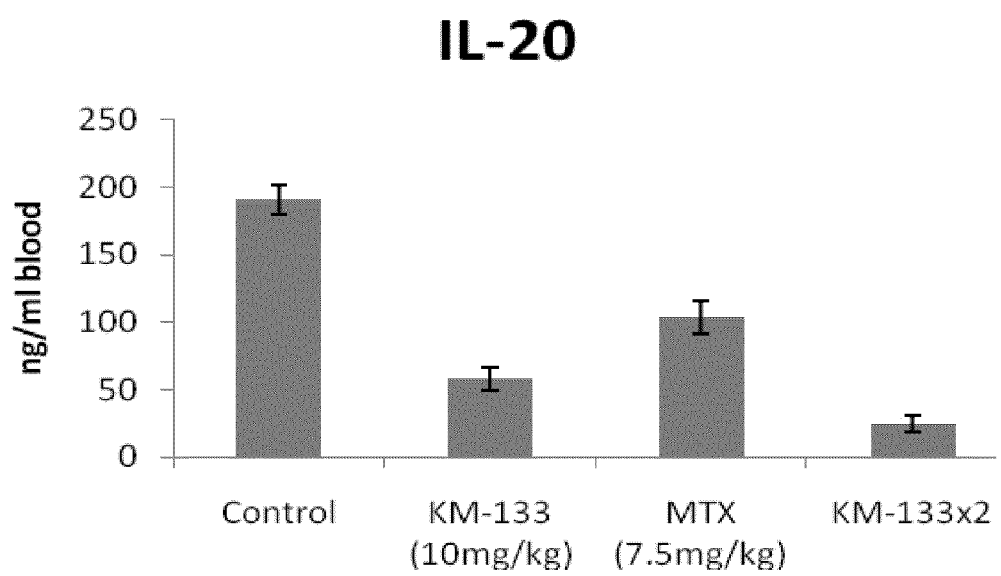
FIG. 1 shows production of IL-20 in mice by Prurisol (at doses of 10 mg/kg or 2×10 mg/kg) and MTX (methotrexate) (at dose 7.5 mg/kg).

The present invention relates to compounds of the formula

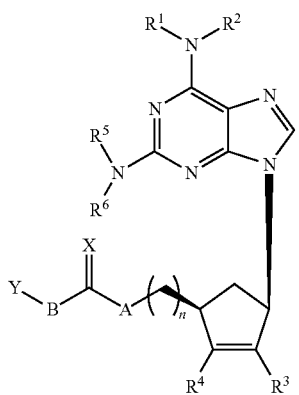

I wherein $R^1$ and $R^2$ are independently selected from hydrogen, $CO_2C_1$-$C_4$ alkyl, $C_1$-$C_6$ alkyl, $C_2$-$C_6$ alkenyl and $C_2$-$C_6$ alkynyl, wherein the alkyl moieties of said alkyl, alkenyl, and alkynyl groups may be linear, branched chain or a combination of linear and branched chain,

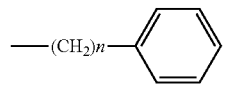

where n is 0 to 3,

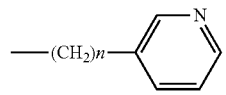

where n is 1 to 2, $C_3$-$C_7$ cycloalkyl, a three to twelve membered heterocyclic ring containing up to 3-heteroatoms where the heteroatoms are independently selected from O, N or S and where each heterocyclic ring may be optionally substituted at one or more carbon atoms by from 1 to 3-substituents independently selected from $C_1$-$C_6$ alkoxy, and O—$C_1$-$C_6$ alkyl;
$R^3$ and $R^4$ are independently selected from hydrogen and $C_1$-$C_6$ alkyl;
$R^5$ and $R^6$ are independently selected from hydrogen and —$CO_2C_4H_9$;
A is selected from a covalent bond, O, S, Se, $C_1$-$C_6$ alkyl, and $(CH_2)_nO$, where n is an integer from 0 to 3;
X is selected from O, S and Se;
B is selected from a covalent bond, —$CH_2$—, —$CH_2$—$CH_2$—, —$CH_2$—$CH_2$—$CH_2$—, trans-CH=CH—, cis-CH=CH—, —C≡C—, —$CHR^7$—$CHR^8$—, cis or trans-$CR^7$=$CR^8$—, wherein $R^7$ and $R^8$ are independently selected from $C_1$-$C_6$ alkyl, $C_2$-$C_6$ alkenyl, $C_2$-$C_6$ alkynyl, and $C_3$-$C_7$ cycloalkyl; and
Y is selected from of OH, SH, $OR^9$ wherein $R^9$ is $C_1$-$C_6$ alkyl, $C_2$-$C_6$ alkenyl and $C_2$-$C_6$ alkynyl, $C_3$-$C_7$ cycloalkyl, and $(CH_2)_nOH$, wherein n is an integer from 1 to 6 and $NR^9R^{10}$ wherein $R^9$ and $R^{10}$ are independently selected from $C_1$-$C_6$ alkyl and $C_3$-$C_7$ cycloalkyl;
and the pharmaceutically acceptable salts thereof.

In the above formula, it should be understood that when B is a covalent bond, Y is connected by said covalent bond to the carbon that is connected to both X and to A.

One embodiment of the present invention relates to (−) cis-[4-[2-amino-6-(cyclopropylamino)-9H-purin-9-yl]-2-cyclopentene-1-hydroxymethyl acetate (Prurisol) and the pharmaceutically acceptable salts thereof.

One embodiment of the present invention relates to a pharmaceutical composition for the treatment of inflammatory skin disease, such as psoriasis, eczema and seborrhiasis, comprising a compound of the formula I as defined in any one of the above embodiments and a pharmaceutically effective carrier.

Another embodiment of the present invention relates to a pharmaceutical composition for the treatment of inflammatory skin disease, such as psoriasis, eczema and seborrhiasis, comprising an anti-inflammatory effective amount of a compound of the formula I as defined in any one of the above embodiments and a pharmaceutically effective carrier. In one embodiment the compound is (−) cis-[4-[2-amino-6-(cyclopropylamino)-9H-purin-9-yl]-2-cyclopentene-1-hydroxymethyl acetate (Prurisol) or a pharmaceutically acceptable salt thereof.

Other embodiments of the present invention relate to a pharmaceutical composition for the treatment of psoriasis comprising an anti-psoriasis effective amount of a compound of the formula I as defined in any one of the above embodiments and a pharmaceutically effective carrier.

Another embodiment of the invention relates to a method of treating an inflammatory skin disease, such as psoriasis, eczema and seborrhiasis, comprising administering to a patient in need of such treatment an anti-inflammatory effective amount of a compound of formula I or a pharmaceutically acceptable salt thereof. In one embodiment of the invention the inflammatory skin disease is selected from psoriasis, eczema and seborrhiasis Another embodiment of the invention relates to a method of treating an inflammatory skin disease in a patient in need of such treatment comprising administering to said patient an amount of a compound according to claim 1 effective to treat said disease.

Another embodiment of the invention relates to a method of treating psoriasis comprising administering to a patient in need of such treatment an antipsoriasis effective amount of a compound of formula I or a pharmaceutically acceptable salt thereof.

In other embodiments of the invention the compositions are topical compositions.

In other embodiments of the invention the compositions are in the form of a unit dose.

The pharmaceutically acceptable salts of the compounds of formula I include the acid addition and base salts (including disalts) thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, dibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula I may be readily prepared by mixing together solutions of the compound of formula I and the desired acid or base, as appropriate. The salt may precipitate from solution and be collected by filtration or may be recovered by evaporation of the solvent. The degree of ionization in the salt may vary from completely ionized to almost non-ionized.

The compounds of formula I and the pharmaceutically acceptable salts thereof (hereinafter also referred to as the active compounds) may exist in both unsolvated and solvated forms. The active compounds (including, those in the form of salts, free bases, free acids and neutral compounds) may form hydrates and other solvates. The term "solvate" is used herein to describe a molecular complex comprising a compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. The active compounds may exist as clathrates or other complexes. In general, the solvated, hydrated and the like forms are equivalent to the unsolvated, unhydrated/anhydrous and the like forms and the compounds, compositions and uses claimed herein are intended to encompass these forms, as well as the isomeric, crystalline and amorphous forms and the isotopically labeled compounds discussed below, within the scope of the present invention.

Compounds of formula I containing one or more asymmetric carbon atoms can exist as two or more stereoisomers. Where a compound of formula I contains an alkenyl or alkenylene group or a cycloalkenyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism. The compounds of formula I may also exist as isomers if they form acid addition or base salts wherein the counterion is optically active, for example, D-lactate or L-lysine, or racemic, for example, DL-tartrate or DL-arginine.

Mixtures of stereoisomers may be separated by conventional techniques known to those skilled in the art. See, for example, "Stereochemistry of Organic Compounds" by E. L. Eliel (Wiley, New York, 1994).

Cis/trans isomers may be separated by conventional techniques well known to those skilled in the art, for example, chromatography and fractional crystallization.

In general, enantiomerically pure compounds of the present invention can be prepared and can be isolated according to art-known processes such as, for example, chiral synthesis from a suitable optically pure precursor and resolution of a racemate (or a racemate of a salt or derivative). For example, a racemate (or a racemic precursor) may be separated using chiral high pressure liquid chromatography (HPLC). Alternatively, a racemate (or a racemic precursor) may be reacted with a suitable optically active compound, for example, an alcohol, or, in the case where the compound of formula I contains an acidic or basic moiety, with an acid or base such as tartaric acid or 1-phenylethylamine. The resulting diastereomeric mixture may be separated by chromatography or fractional crystallization or both and one or both of the diastereoisomers may be converted to the corresponding pure enantiomer(s) by means well known to a skilled person.

Chiral compounds of the present invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

In the solid state, the compounds of the present invention may exist in crystalline or amorphous form.

The present invention includes all pharmaceutically acceptable isotopically-labelled compounds of formula I claimed herein wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying Examples using an appropriate isotopically-labeled reagent in place of the non-labeled reagent previously employed.

The present invention also relates to a process for preparing a compound of the formula I wherein $R^1$ and $R^2$ are a hydrogen and a cyclopropyl group, respectively, as defined above for formula I by reacting compound 4 (shown in Scheme II below) with (tert-butyldimethylsilyloxy)acetyl chloride, followed by acid treatment and, if desired, preparing the free base or a different acid addition salt.

In one embodiment of the invention the solvent is selected from triethyl amine or diisopropylethyl amine or N-methyl morpholine.

In one embodiment of the invention the hydrobromide acid addition salts are prepared by substituting a bromine containing starting material in the processes described above. The mesylate salts are prepared by substituting a mesylate starting material in the processes described above. A disalt of the present invention may be similarly prepared by using a salt as the starting material. It may be possible to form such a salt if the free base has two basic centers.

One embodiment of the present invention, relates to a pharmaceutical composition for the treatment of psoriasis, eczema and seborrhiasis and other inflammatory skin diseases comprising (−) cis-[4-[2-amino-6-(cyclopropylamino)-

9H-purin-9-yl]-2-cyclopentene-1-hydroxymethyl acetate (Prurisol). The chemical structure of Prurisol is shown below (see formula 9). It is highly orally bioavailable (% F=83%) compound and is metabolized primarily through alcohol dehydrogenase or glucuronyl transferase. It is also capable of crossing the blood brain barrier. It is stable and is stored at ambient temperature and protected from light. As discussed below, (−) cis-[4-[2-amino-6-(cyclopropylamino)-9H-purin-9-yl]-2-cyclopentene-1-hydroxymethyl acetate (Prurisol) has demonstrated significant activity against psoriasis in animal models.

DETAILED DESCRIPTION OF THE INVENTION

The following reaction schemes illustrate the preparation of Prurisol.

Scheme I

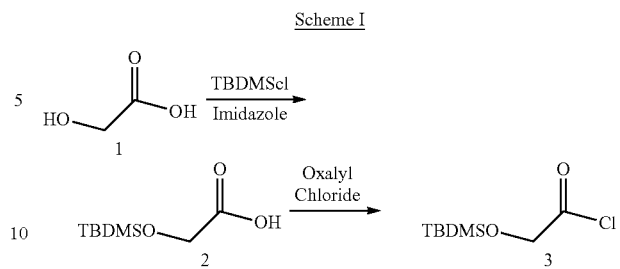

Scheme I shows the preparation of tert-butyldimethylsilyloxy acetyl chloride. Glycolic acid on reaction with TBDMS-Cl (tert-butyldimethylsilyloxy chloride) in the presence of imidazole provided O-tert-butyldimethylsilyloxy acetic acid, which on reaction with oxalyl chloride gave the desired acid chloride derivative.

Scheme II

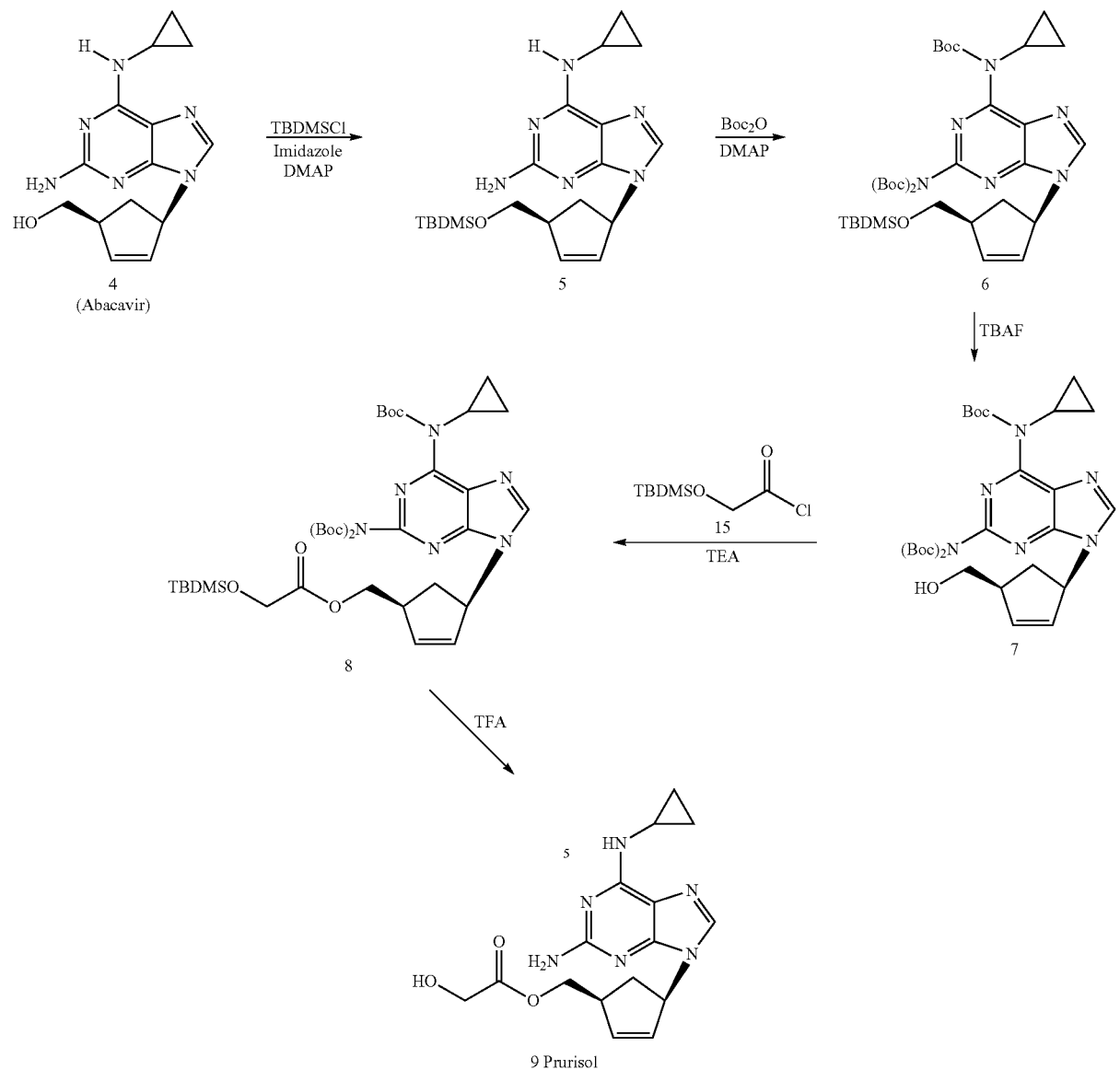

Scheme II shows synthesis of Prurisol. The starting material Abacavir (4) can be easily prepared by the literature method [Crimmins, et. al., J. Org. Chem., 61, 4192-4193 (1996) and 65, 8499-8509-4193 (2000)], which on treatment with TBDMS-Cl as described above gave O-tert-butyldimethylsilyloxy derivative (5). Compound 5, on reaction with di-tert-dibutyl carbonate, afforded a good yield of compound (6), which following treatment with tetrabutylammonium fluoride provided desired key intermediate 7. This compound, on reaction with compound 3, gave protected ester 8, which followed by deprotection with acid gave compound 9 (Prurisol).

One of ordinary skill in the art would know how to select conditions from those discussed above or to make modifications thereto in order to make other specific compounds of the Formula I that are of interest, including compounds wherein $R^1$ and $R^2$ are other than a hydrogen and compounds wherein $R^2$ is other than a cyclopropyl group.

The present invention also includes a method of inhibiting psoriasis which is a chronic, autoimmune disease that appears on the skin. The method includes contacting the skin cells with compound formula I in a sufficient amount to inhibit the growth cycle. In general, formula I is useful in treating the inflammatory diseases of the skin including eczema, sclerodermatitis and seborrhiasis. The compounds herein described can form the active ingredient of a pharmaceutical composition, and are typically administered in admixture with suitable excipients or carriers suitably selected are oral tablets or capsules. The dosage compositions such as tablets, capsules, pills, suppositories and powders depend on the intended mode of administration, which can be via any acceptable route. These routes of administration include oral, local, transdermal, subcutaneous and nasal. One or more of these routes can be used in a single patient. The compounds of the invention preferably can be used as oral dosage form for the administration and can be combined with non-toxic pharmaceutically acceptable inactive carriers such as water, glycerol, ethanol and like. The inert excipients, which are commonly used as binders, disintegrating agents, and coloring agents can also be incorporated into mixture for oral administration If necessary, the pharmaceutical composition to be administered may also contain minor amounts of nontoxic substances such as pH buffering agents, emulsifying agents, sodium acetate etc. The dosage regimen of utilizing the compounds will depend on species, sex, weight, age, medical conditions of patient, the route of administration and the severity of the condition to be treated. A skilled physician can readily determined and prescribe the effective dosage of drug to treat the disease.

Depending on the disease and condition of the patient, the term "treatment" as used herein may include one or more of curative, palliative and prophylactic treatment. The precise dosage administered of each active compound will vary depending upon a number of factors, including but not limited to, the type of patient and type of disease state being treated, the age of the patient, and the route(s) of administration.

For administration to human patients, the total daily dose of the active compounds is anticipated to be in the range of 1 mg to 100 mg per kg of body weight, depending on the mode of administration. For example, oral administration may require a total daily dose of from 10 mg to 100 mg per kg of body weight. The total daily dose may be administered in single or divided doses. For an average human subject having a weight of about 70 kg, the dosage would be about 70 mg to 7000 mg for oral administration. The physician will readily be able to determine doses for subjects whose weight falls outside this range, such as infants and the elderly. A veterinarian will readily be able to determine doses for other mammals.

In one embodiment, the invention comprises administration of an oral administration by means of gelatin capsule or suspension comprising 10 mg of an active compound per kg of body weight. For the above-mentioned therapeutic uses, the dosage administered will, of course, vary with the compound employed, the mode of administration, the treatment desired and the disorder indicated. The total daily dose may be administered in single or divided doses. The present invention also encompasses sustained release compositions.

The pharmaceutical composition may, for example, be in a form suitable for oral administration as a tablet, capsule, pill, powder, sustained release formulation, solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and an active compound. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for preparing tablets. Solid compositions of a similar type may also be employed in soft and hard filled gelatin capsules. Useful components of these compositions include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intrapatient dose-escalation as determined by the skilled artisan. Determining appropriate dosages and regimens for administration of the chemotherapeutic agents are well-known in the relevant art and would be understood to be encompassed by the skilled artisan once provided the teachings disclosed herein.

Psoriasis is an autoimmune disease. Systemic administration of drug is a preferred mode of administration of drug. This autoimmune disease causes lesions in skin causing itching and pruritis. Since this can cause degeneration of tissue, a topical application of the drug may include an emollient. On systemic administration, the level of drug in the tissue is deciding factor, therefore it can be administered BID or TID.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active compound. The amount of the active compound is generally equal to the dosage of the active compound which would be administered to a subject or a convenient fraction of such a dosage such as, for example, one-half or one-third of such a dosage.

The relative amounts of the active compound, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Since the compounds of the present invention may be administered both orally as well as topically (for example, as a cream or ointment) the administered dosage will vary based on the mode of administration. In one embodiment, an oral composition is administered at a dosage of 5 mg/kg/day as a single dose or 10 mg/kg/day as a single dose or multiple doses of such strengths may be administered twice per day, three times per day or four times per day according to the severity of conditions. In one embodiment, if the compound of the present invention is administered as a cream, a proposed percentage of the compound is 10% by weight of the cream and this would result in a dose of about 10 mg/100 g of cream applied ad libitum. In one embodiment, an over the counter (OTC) product would contain a percentage of a compound of the present invention at a concentration of 2% by weight of the cream and this would result in a dose of about 2 mg/100 mg of cream applied ad libitum.

In addition to the active compound, a pharmaceutical composition of the invention may further comprise one or more additional therapeutically effective compounds as discussed above.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. Thus, the active compounds may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous, and kidney dialytic infusion techniques. Suitable devices for such parenteral administration include needle (including microneedle) injectors, needle-free injectors and infusion apparatus.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Figure 2:
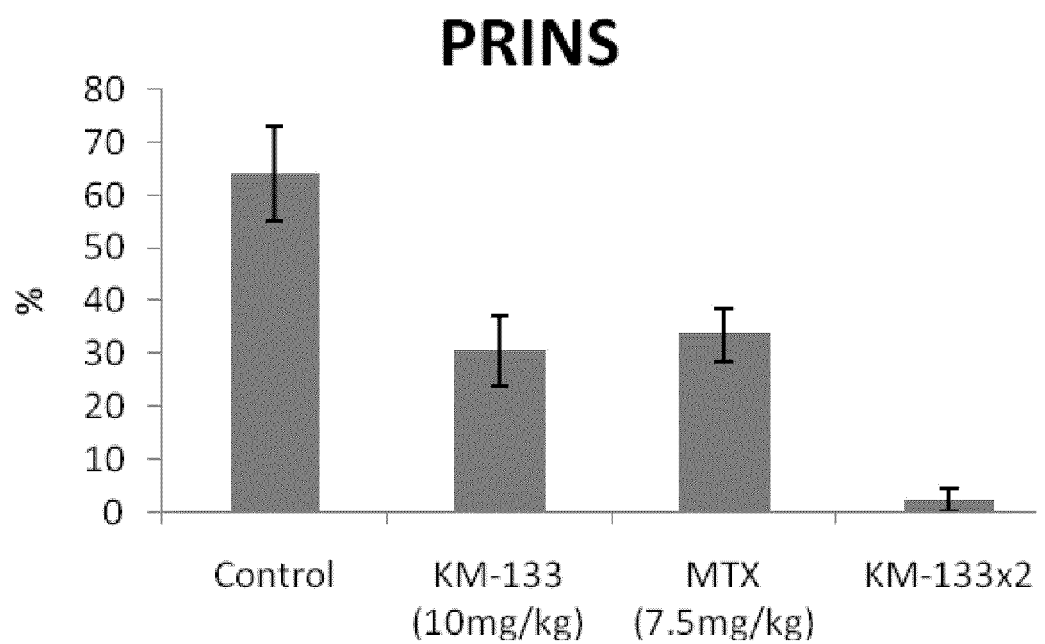
FIG. 2 shows suppression of psoriasis susceptibility related RNA gene induced by stress (PRINS) after administering Prurisol (at doses of 10 mg/kg or 2×10 mg/kg) and MTX (7.5 m/kg).

General Methods:

The following non-limiting Examples illustrate the preparation of the novel compounds and their use in the treatment of inflammatory skin diseases. $^1$HNMR spectra were obtained from a Varian 300 MHz spectrophotometer and chemical shift values are reported in parts per million (ppm, δ) downfield from tetramethylsilane using conventional abbreviations for designation of major peaks: e.g. s, singlet; d, doublet; t, triplet; q, quartet; m, multiplet; br, broad. TLC analysis was carried out on precoated TLC plates with silica gel 60F254 [E Merck]. All intermediates and final compounds were characterized by $^1$HNMR and LCMS spectral data. Purity was checked by HPLC, and overall synthetic strategies for the preparation of (−) cis-[4-[2-amino-6-(cyclopropylamino)-9H-purin-9-yl]-2-cyclopentene-1-hydroxymethyl acetate (Prurisol) is shown in FIG. 2. The mass spectra (m/z) were recorded on an Agilent model 1100 mass spectrometer using either electrospray ionisation (ESI) or atmospheric pressure chemical ionization (APCI). The following abbreviations have been used for common solvents: $CDCl_3$ deuterochloroform; $D_6$-DMSO deuterodimethylsulphoxide; $CD_3OD$ deuteromethanol.

EXAMPLES

Example 1

A. Synthesis of (tert-butyldimethylsilyloxy)acetyl chloride

1. To a stirred solution of hydroxyacetic acid (1.0 g, 13.16 mmol) and tert-dimethylsilyl chloride (4.32 g, 28.80 mmol) in dimethylformamide (DMF) (10 mL), imidazole (3.73 g, 54.91 mmol) was added and resulting reaction mixture was stirred under $N_2$ for 18 hours. Then mixture was poured onto water (100 mL) and compound was extracted with hexane (3×25 mL). The combined hexane layer washed with saturated $NaHCO_3$ solution, and dried over $MgSO_4$. Organic layer on evaporation gave 2.94 g (73%) of a white color solid.

2. To a solution of (tert-butyldimethylsiloxy)acetic acid tert-butyldimethylsilyl ester (2.01 g, 6.61 mmol) in dichloromethane (10 mL) containing 4-drops of DMF, a solution of oxalyl chloride (1.05 g, 8.26 mmol) was added slowly under $N_2$ for 40 minutes. The resulting reaction mixture was stirred at room temperature for 1 hour. The resulting reaction mixture, on evaporation, afforded 1.37 g of yellow colored residue in almost quantitative yield, which was used, as such, for the next step.

B. (−) cis-[4-[2-amino-6-(cyclopropylamino)-9H-purin-9-yl]-2-cyclopentenene-1-O-(tert-butyldimethylsilyloxy)methyl ether A mixture of abacavir (6.0 g, 20.98 mmol), tert-butylsimethylsilyl chloride (3.78 g, 25.20 mmol) and 4-dimethylaminopyridine (DMAP) (0.13 g, 1.05 mmol) in dichloromethane (100 mL) was stirred over night at room temperature. Then an additional amount of tert-butylsimethylsilyl chloride (0.63 g, 4.2 mmol) was stirred and reaction was continued for 1.5 hours. Then a saturated $NaHCO_3$ (100 mL) solution was added and layer was separated. The organic layer was washed with brine (100 mL), and dried over $MgSO_4$. Dichloromethane was removed under reduced pressure and the residue was purified by a CombiFlash™ System with a RediSep™ column with silica gel as a solid support, using a hexane/ethyl acetate mixture (100-5:0-95) as the eluant, to give 5.55 g (66.15%) of desired product which was used, as such, for the next step.

C. (−) cis-[4-[2-N(bis-butyloxycabonyl)amino-6-(N-butoxycarbonyl, N-cyclopropyl)amino)-9H-purin-9-yl]-2-cyclopentene-1-O-(tert-butyldimethylsilyloxy)methyl ether A mixture of TBDMS derivative (5.55 g, 13.88 mmol), di-tert-butyl dicarbonate (10.59 g, 48.58 mmol) and DMAP (0.17 g, 1.388 mmol) in acetonitrile (170 mL) was stirred at room temperature for 6 hours. Then an additional amount of di-tert-butyl dicarbonate (4.54 g, 20.83 mmol) and DMAP (0.17 g, 1.388 mmol) were added and resulting reaction mixture was stirred at room temperature for 48 hours. Then solvent was removed and residue was dissolved in dichloromethane (100 mL). The organic layer was washed with saturated $NaHCO_3$ (100 mL), and then with brine (100 mL), and then dried over $MgSO_4$. The organic layer was then evaporated and the resulting residue was purified using a CombiFlash™ System with a RediSep™ column with silica gel as a solid support, using a hexane/ethyl acetate mixture (100:00 to 70:30) as the eluant, to give 4.40 g (45.30%) of product.

D. (−) cis-[4-[2-N(bis-butyloxycabonyl)amino-6-(N-butoxycarbonyl, N-cyclopropyl)amino)-9H-purin-9-yl]-2-cyclopentene-1-methanol To an ice-cold stirred solution of O-(tert-Butyldimethylsilyloxy)-N,N,N-tributoxycarbonylabacavir (4.40 g, 6.29 mmol) in tetrahydrofuran (100 mL), a solution of tetrabutylammonium fluoride (TBAF) in tetrahydrofuran (4.5 mL, 9.43 mmol) was added. The resulting reaction mixture was allowed to warm to room temperature, and stirring was continued for 1 hour. The solvent was then evaporated and the residue was suspended in ethyl acetate (100 mL) and washed with 1N $NaHSO_4$ (100 mL), then with saturated $NaHCO_3$ (100 mL), and then with brine (100 mL), and then dried over $MgSO_4$. The organic layer was then evaporated and the resulting residue was purified by a CombiFlash™ System with a RediSep™ column with silica gel as a solid support, using a hexane/ethyl acetate mixture (100:00 to 00:100) as the eluant to give 3.51 g (95.38%) of product.

E. (−) cis-[4-[2-N(bis-butyloxycabonyl)amino-6-(N-butoxycarbonyl, N-cyclopropyl)amino)-9H-purin-9-yl]-2-cyclopentene-1-(O-tert-butyldimethylsilyloxy)methyl acetate To a stirred ice cold solution of the title compound of step D above (1.02 g, 1.74 mmol) and triethylamine (TEA) (5 mL) in dichloromethane (100 mL), O-tert-butyldimethylsilyloxyacetyl chloride (0.36 g, 1.73 mmol) was added dropwise. The resulting reaction mixture was stirred for 1 hour and then saturated $NAHCO_3$ solution (100 mL) was added. The dichloromethane layer was separated, washed with brine, and dried over $MgSO_4$. The organic layer was evaporated to dryness, and the resulting residue was purified by a CombiFlash™ System with a RediSep™ column with silica gel as a solid support, using a hexane/ethyl acetate mixture (100:00 to 60:40) as the eluant, to give 0.38 g (28.78%) of product.

F. (−) cis-[4-[2-amino-6-cyclopropylamino)-9H-purin-9-yl]-2-cyclopentene-1-hydroxymethyl acetate (Prurisol)

To a stirred ice cold solution of O-(tert-butyldimethylsliloxy)acetyloxy-N,N,N-tributoxycarbonylabacavir (0.38 g, 0.50 mmol) in dichloromethane (30 mL), trifluoroacetic acid (TFA) (12 mL) was added and mixture was allowed to warm to room temperature for 1 hour. Then solvent was removed, and acetonitrile (30 mL) was added, followed by addition of 40% TFA in water (4.5 mL). The resulting reaction mixture was stirred at room temperature for one hour, then acetonitrile was evaporated under reduced pressure, and dichloromethane (30 mL) and saturated $NaHCO_3$ solution were added. The organic layer was separated, dried over $MgSO_4$ and evaporated to dryness. The resulting residue was purified by a CombiFlash™ System with a RediSep™ column with silica gel as a solid support, using a dichloromethane/methanol mixture (100:00 to 94:6) as the eluant, to give 0.132 g (75.43%) of final product. $^1H$ NMR (DMSO-$d_6$, free base) $\square_H$ 0.45-0.76 (4H, m, $CH_2$), 1.58 (1H, m, CH), 2.65 (1H, m, CH), 2.92-3.18 (2H, m, $CH_2$), 3.98 (2H, dd, $CH_2$), 4.13 (2H, d, $CH_2$), 5.30 (1H, t, CH), 5.39 (1H, m, CH), 5.80 (2H, bs, $NH_2$), 5.93 (1H, dt, CH), 6.06 (1H, dt, CH), 7.27 (1H, d, NH), 7.78 (1H, s, Ar—H); mass ($C_{16}H_{20}N_6O_3$, 344.37) found (m+1) 345.1.

Example 2

In Vivo Efficacy of Prurisol in Animal Models

Psoriatic Tissue and Mice

In order to examine efficacy of the (−) cis-[4-[2-amino-6-(cyclopropylamino)-9H-purin-9-yl]-2-cyclopentene-1-hydroxymethyl acetate in mice, male and female SCID mice (24 to 28 gms) 6 to 8 weeks old were purchased from Charles River Laboratory (Wilmington, Mass.). The animals were kept in standard rodent cages with isolator tops at 18-26° C., and a relative humidity of 30-70% on a 12 hour light/12 hour dark cycle. Mice were given rodent chow and water ad libitum. Animals were acclimated for a period of one week and each animal was observed at least once daily for any abnormalities or for the development of infectious disease. Suitable animals were selected for the assigned study.

Any animals considered unacceptable for use in this study were replaced with animals of similar age and weight from same vendor. Human psoriatic tissues were purchased from National Disease Research Interchange, Philadelphia, Pa.

Total Body Irradiation (TBI)

Mice were subjected to total body irradiation to mildly suppress immune system at 120 rads per animal in a Gamma Cell Radiator. Mice were identified by ear punching.
Implantation of Psoriatic Tissue 24 Hours after the TBI, a 5 mm×5 mm cut of the human psoriatic tissue was transplanted on the skin of the mice, under ketamine/xylazine anesthesia. The tissues were adherent by using a skin cement. All animals survived the anesthesia and the surgery for the experiment. The complete fusion of the tissues was achieved by day 27. During treatments, mice were observed daily for any adverse affects. Mice body weights were taken prior to treatment and every other day during the post treatment. If an animal became unwell, any treatment of that animal was suspended. If there was no recovery, the animal was sacrificed. An animal demonstrating more than 15% weight loss was considered unwell. Any animal that demonstrated a weight loss greater than 20% was sacrificed. Any animals exhibiting sustained ulceration of the skin over the site were sacrificed. Mice transplant area size measurements were taken prior to treatment and every other day during and post treatment. The same scientist was responsible for taking the measurements throughout the study.

Once a transplant site from the vehicle group reached a clinically intolerable condition to the animals, all animals from the entire group reached were sacrificed by $CO_2$ asphyxiation. Upon sacrifice, transplant sites were removed and analyzed.

In Vivo Efficacy Protocols

Groups of 5 male mice and 5 female mice bearing psoriatic tissues were treated with either (−) cis-[4-[2-amino-6-(cyclopropylamino)-9H-purin-9-yl]-2-cyclopentene-1-hydroxymethyl acetate (Prurisol) alone or methotrexate (MTX) according to the schedule below. Another group of mice remained untreated to serve as controls.

Data are presented as median volume over time. Treatment efficacy is analyzed in 3 ways. Firstly, individual psoriatic tissue volumes are compared at a single time point. Secondly, the number of days for each tissue to reach a predetermined end point size, i.e., time to endpoint (TTE) is analyzed. If data are normally distributed, then a two-tailed statistical analysis at $p=0.05$ using Mann-Whitney-Wilcoxon Rank Sum test is used to determine significant differences between groups. Thirdly, psoriatic growth is calculated as the difference between the median TTE for the treatment group and median TTE of the control group expressed as a percentage of the control group.

Results

Weight Changes

Prurisol was administered orally (PO) to the mice, along with the topical application at 8 hour intervals on the effected area. The weight loss due to the administration of compound was within acceptable limits. 5 mg/kg administered on days 11 to 35, and 20 mg/kg in the schedule topically resulted in no weight loss, which suggested that Prurisol is not toxic. In psoriasis, anti-apoptotic protein G1P3 is over expressed, which is regulated by the non-coding RNA. Psoriasis susceptibility related RNA Gene Induced by Stress (PRINS) was examined in control animal's transplants and treated ones (the expression in psoriatic plaques will be 10 times higher), and results from these studies are shown below.

| Subject | PRINS |
|---|---|
| Control | 49 |
| Prurisol | 24 |
| MTX | 28 |
| Prurisol × 2 | 5 |

Results from this study demonstrated that Prurisol reduces PRINS significantly in comparison to methotrexate (MTX). IL-20 was also measured using ELISA technique and data is also shown below.

| Control | 178 |
|---|---|
| Prurisol | 54 |
| MTX | 127 |
| Prurisol × 2 | 18 |

Figure 3:
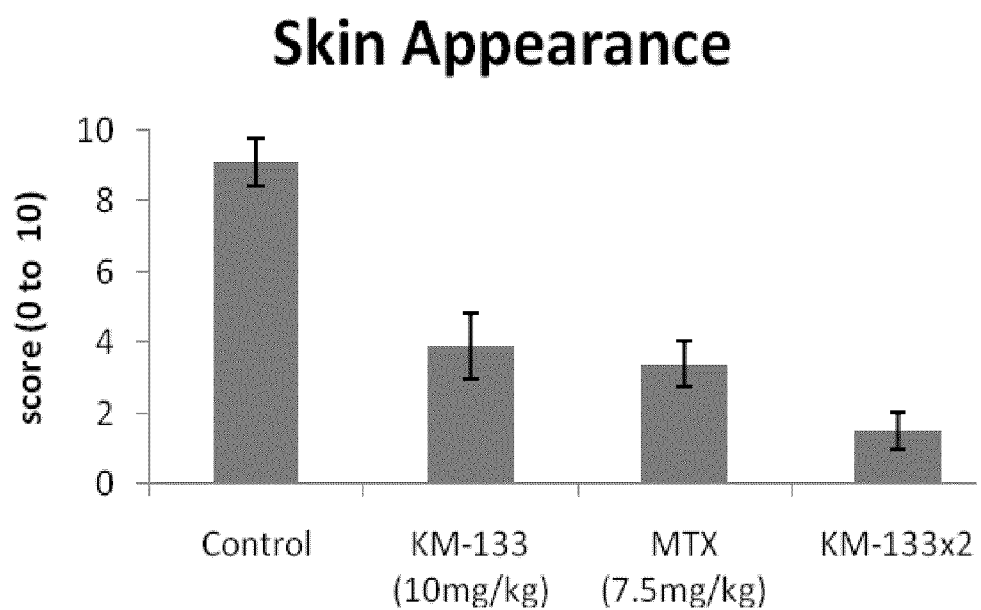
FIG. 3 shows appearance of skin after administration of Prurisol and MTX.

The above results indicate that Prurisol and methotrexate reduce concentration of IL-20 in tissue by 3 fold and 1.4 fold, respectively. Overall, these results suggest that prurisol is more effective than methotrexate in controlling psoriasis. The above results are also depicted in FIGS. 1, 2 and 3.

Figure 4:
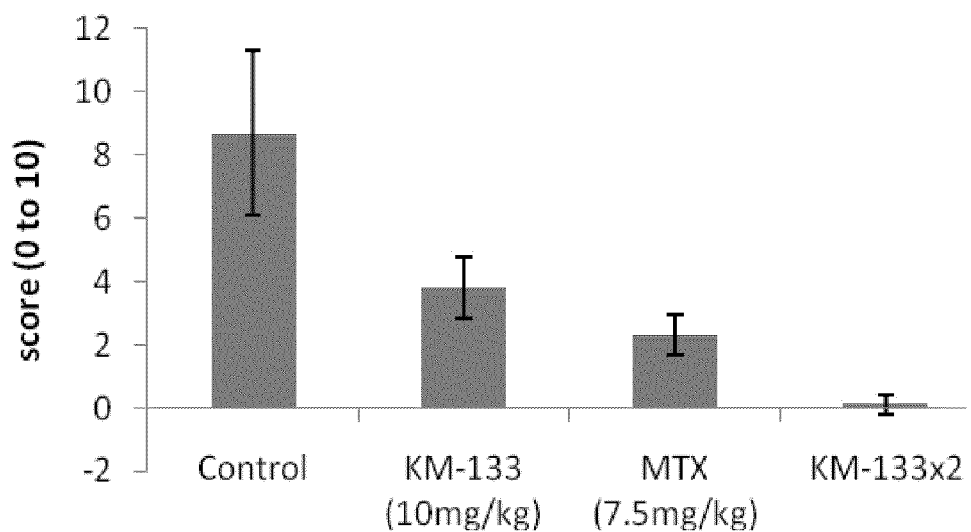
FIG. 4 shows Normalization of skin in histological parameters compare to fully psoriatic skin and MTX

Lesions or skin area where the xenografts were implanted were dissected out aseptically. Under a microtome, 0.5 uM thick slides were prepared and mounted on glass. Specimens were treated in ascending percentages of alcohol, up to 100%, each time holding the specimen in a particular percentage of alcohol for two hours. Specimens were then dried and stained with hematoxylin and Eosin. Slices were examined under a LEICA™ microscope under 20×. The slides were graded from 1 to 10, 1 being normal tissue, and 10 being very severe psoriasis tissue. The results are shown in FIG. 4.

The 12R-lipoxygenase cDNA is detectable by PCR in psoriatic scales and as a 2.5-kilobase mRNA by Northern analysis of keratinocytes. Identification of this enzyme extends the known distribution of R-lipoxygenases to humans and presents an additional target for potential therapeutic interventions in psoriasis, and the results when animals were dosed at 10 mg/kg are illustrated below in FIG. 5.

Figure 5:
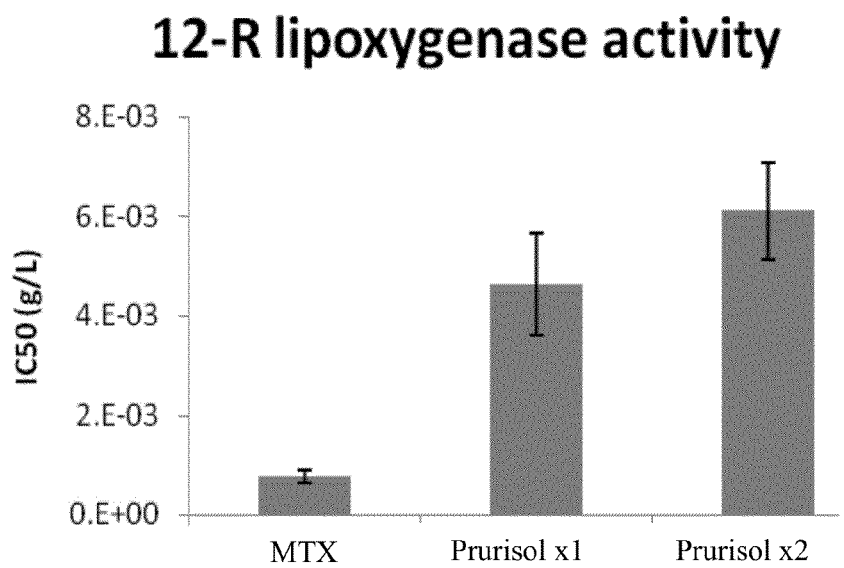
FIG. 5 shows induction of 12-R lipoxygenase activity by Prurisol and MTX.

FIG. 5 shows induction of 12-R lipoxygenase activity by Prurisol and MTX

Figure 6:
FIG. 6 shows appearance of skin by naked eye in psoriatic animals and those treated with Prurisol.

Severe combined immunodeficiency (SCID) animals were given a total body radiation and implanted with human psoriatic tissue. All the animals were treated either by vehicle, prurisol, 10 mg, either one time per day or BID and MTX. After the treatment, the animals were recovered from psoriasis as the picture in FIG. 6 indicates.

Figure 7:
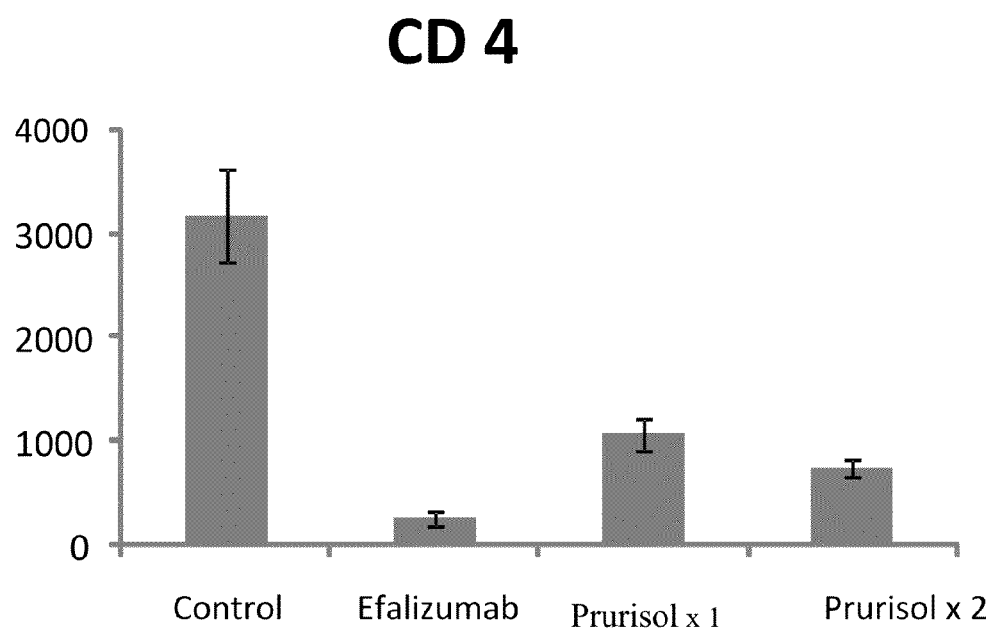
FIG. 7 shows reduction of CD4.
Figure 8:
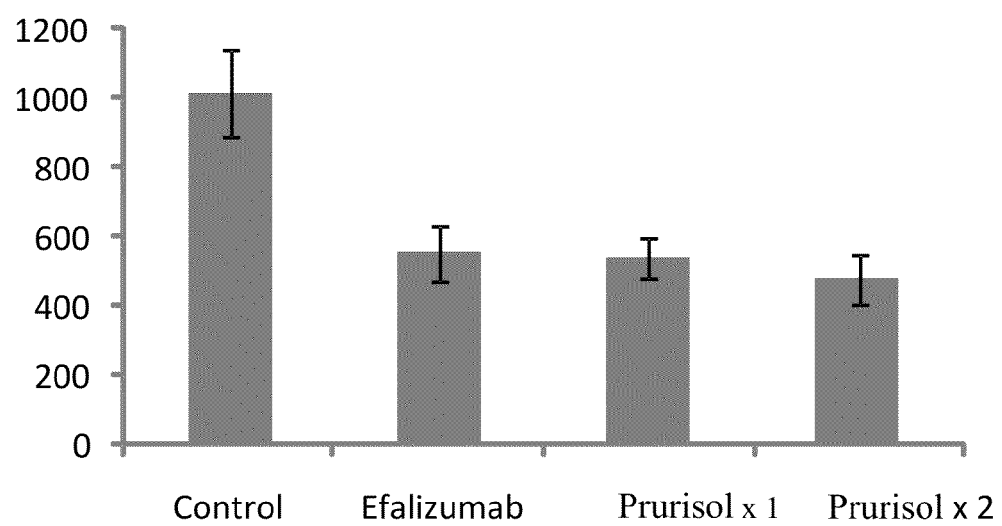
FIG. 8 shows reduction of CD8.

The data shown in FIGS. 7 & 8 for CD4 and CD8, respectively, were obtained by Fluorescence-Activated Cell Sorting (FACS). The terms CD4 and CD8 denote the severity of inhibition of tolerance by the animals. A low CD4 and CD8 level indicates that the animals are getting immunocompromised, if the level goes down below 70% of the original levels then treatment should be stopped. CD4 and CD8 are members of the immunoglobulin superfamily. CD4 and CD8 (cluster of differentiation 4 or 8) are glycoproteins expressed on the surface of T helper cells, monocytes, macrophages, and dendritic cells.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

I claim:

1. A compound of the formula

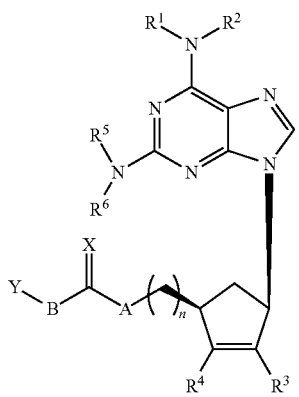

I wherein $R^1$ and $R^2$ are independently selected from hydrogen, $CO_2C_1$-$C_4$ alkyl, $C_1$-$C_6$ alkyl, $C_2$-$C_6$ alkenyl and $C_2$-$C_6$ alkynyl, wherein the alkyl moieties of said alkyl, alkenyl, and alkynyl groups may be linear, branched chain or a combination of linear and branched chain

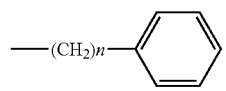

where n is 0 to 3,

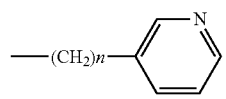

where n is 1 to 2, $C_3$-$C_7$ cycloalkyl, a three to twelve membered heterocyclic ring containing up to 3-heteroatoms where the heteroatoms are independently selected from N, O and S and where each heterocyclic ring may be optionally substituted at one or more carbon atoms by from 1 to 3 substituents independently selected from $C_1$-$C_6$ alkoxy, and O—$C_1$-$C_6$ alkyl;

$R^3$ and $R^4$ are independently selected from hydrogen and $C_1$-$C_6$ alkyl;

$R^5$ and $R^6$ are independently selected from hydrogen and —$CO_2C_4H_9$;

A is selected from a covalent bond, O, S, Se, $C_1$-$C_6$ alkyl, and $(CH_2)_nO$, where n is an integer from 0 to 3;

X is selected from a covalent bond, O, S and Se;

B is selected from a covalent bond, —$CH_2$, —$CH_2$—$CH_2$—, —$CH_2$—$CH_2$—$CH_2$—, trans-CH=CH—, cis-CH=CH—, —C≡C—, —$CHR^7$—$CHR^8$—, cis or trans-$CR^7$=$CR^8$—, wherein $R^7$ and $R^8$ are independently selected from $C_1$-$C_6$ alkyl, $C_2$-$C_6$ alkenyl, $C_2$-$C_6$ alkynyl, and $C_3$-$C_7$ cycloalkyl; and Y is selected from of OH, SH, $OR^9$ wherein $R^9$ is $C_1$-$C_6$ alkyl, $C_2$-$C_6$ alkenyl and $C_2$-$C_6$ alkynyl, $C_3$-$C_7$ cycloalkyl, and $(CH_2)_nOH$, wherein n is an integer from 1 to 6 and $NR^9R^{10}$ wherein $R^9$ and $R^{10}$ are independently selected from $C_1$-$C_6$ alkyl and $C_3$-$C_7$ cycloalkyl;

or a pharmaceutically acceptable salt thereof.

2. A compound having the formula

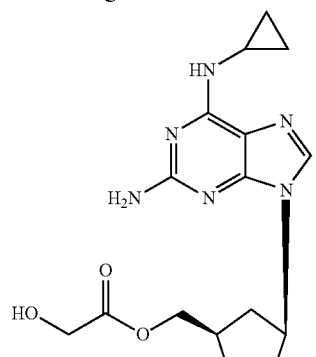

Prurisol or a pharmaceutically acceptable salt thereof.

3. The compound (−) cis-[4-[2-amino-6-cyclopropylamino)-9H-purin-9-yl]-2-cyclopentene-1-hydroxymethyl acetate according to claim 2.

4. A pharmaceutically acceptable salt of the compound (−) cis-[4-[2-amino-6-cyclopropylamino)-9H-purin-9-yl]-2-cyclopentene-1-hydroxymethyl acetate according to claim 2.

5. A pharmaceutical composition for treating inflammatory skin diseases comprising an anti-inflammatory effective amount of a compound according to claim 1 and a pharmaceutically acceptable carrier.

6. A pharmaceutical composition for treating inflammatory skin diseases comprising an anti-inflammatory effective amount of a compound according to claim 2 and a pharmaceutically acceptable carrier.

7. A pharmaceutical composition according to claim 5, wherein said composition is in dosage unit form.

8. A pharmaceutical composition according to claim 6, wherein said composition is in dosage unit form.

9. A pharmaceutical composition for treating psoriasis, eczema, or seborrhiasis comprising an anti-psoriasis, anti-eczema or anti-seborrhiasis effective amount of a compound according to claim 1 and a pharmaceutically acceptable carrier.

10. A method of treating an inflammatory skin disease in a patient in need of such treatment comprising administering to said patient an amount of a compound according to claim 1 effective to treat said disease.

11. A method according to claim 10, wherein said compound is (−) cis-[4-[2-amino-6-(cyclopropylamino)-9H-purin-9-yl]-2-cyclopentene-1-hydroxymethyl acetate (Prurisol) or a pharmaceutically acceptable salt thereof.

12. A method according to claim 10, wherein said inflammatory disease is psoriasis.

13. A method according to claim 12, wherein said compound is (−) cis-[4-[2-amino-6-(cyclopropylamino)-9H-purin-9-yl]-2-cyclopentene-1-hydroxymethyl acetate (Prurisol).

14. A method according to claim 10, wherein said inflammatory disease is eczema.

15. A method according to claim 14, wherein said compound is (−) cis-[4-[2-amino-6-(cyclopropylamino)-9H-purin-9-yl]-2-cyclopentene-1-hydroxymethyl acetate (Prurisol).

16. A method according to claim 10, wherein said inflammatory disease is seborrhiasis.

17. A method according to claim 16, wherein said compound is (−) cis-[4-[2-amino-6-(cyclopropylamino)-9H-purin-9-yl]-2-cyclopentene-1-hydroxymethyl acetate (Prurisol).

18. A compound of the formula

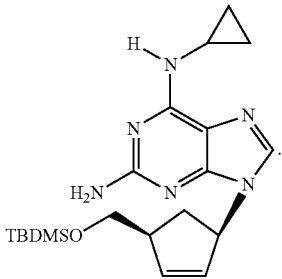 [SMILES: CC(C)(C)[Si](C)(C)OC[C@@H]1C=C[C@H](n2cnc3c(NC4CC4)nc(N)nc32)C1]

19. A compound of the formula

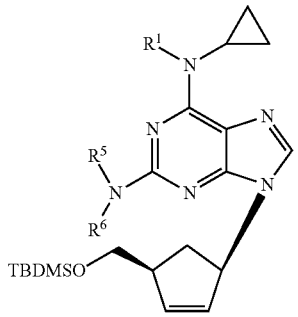

wherein $R^1$, $R^5$ and $R^6$ are independently selected from the group consisting of hydrogen and —$CO_2C_4H_9$.

20. A compound of the formula

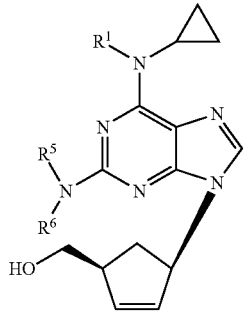

wherein $R^1$, $R^5$ and $R^6$ are independently selected from the group consisting of hydrogen and —$CO_2C_4H_9$.

21. A compound of the formula

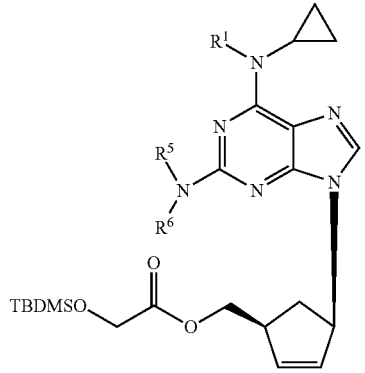

wherein $R^1$, $R^5$ and $R^6$ are independently selected from the group consisting of hydrogen and —$CO_2C_4H_9$.

* * * * *